US006291706B1

(12) United States Patent
Sumner, Jr. et al.

(10) Patent No.: US 6,291,706 B1
(45) Date of Patent: Sep. 18, 2001

(54) HYDROGENATION OF PHTHALIC ACIDS TO CYCLOHEXANEDICARBOXYLIC ACID

(75) Inventors: Charles Edwan Sumner, Jr.; Bruce LeRoy Gustafson, both of Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/335,198

(22) Filed: Jun. 17, 1999

(51) Int. Cl.[7] .................................................. C07C 61/09
(52) U.S. Cl. .......................... 562/433; 562/509; 502/313
(58) Field of Search ................................. 562/433, 509; 502/313; 509/313

(56) References Cited

U.S. PATENT DOCUMENTS

| 2,675,390 | 4/1954 | Rosenblatt | 260/514 |
|---|---|---|---|
| 2,828,335 | 3/1958 | Ferstandig et al. | 260/514 |
| 3,444,237 | 5/1969 | Jaffe et al. | 260/468 |
| 3,584,039 | * 6/1971 | Meyer | 260/525 |
| 4,754,064 | 6/1988 | Lillwitz | 562/509 |
| 5,118,841 | 6/1992 | Cook et al. | 562/509 |
| 5,202,475 | 4/1993 | Cook et al. | 562/509 |

FOREIGN PATENT DOCUMENTS

| 0 603 825 | 6/1994 | (EP) . |
|---|---|---|
| 833185 | 4/1960 | (GB) . |
| 58 198439 | 11/1983 | (JP) . |

OTHER PUBLICATIONS

Low–Pressure Hydrogenation of Some Benzenepolycarboxylic Acids with Some Rhodium Catalyst, J. Org. Chem., vol. 31, Oct. 1966, pp., 3438–3439.

* cited by examiner

Primary Examiner—Paul J. Killos
(74) Attorney, Agent, or Firm—Rose M. Allen; Harry J. Gwinnell

(57) ABSTRACT

The present invention relates to an improved process for the hydrogenation of phthalic acids over a supported palladium catalyst. Phthalic acids are hydrogenated with improved selectivity in aqueous solution over palladium on carbon catalyst to give cyclohexanedicarboxylic acids (CHDA).

6 Claims, No Drawings

HYDROGENATION OF PHTHALIC ACIDS TO CYCLOHEXANEDICARBOXYLIC ACID

BACKGROUND OF THE INVENTION

This invention relates to the conversion of phthalic acids to cyclohexanedicarboxylic acids by catalytic hydrogenation. Cyclohexanedicarboxylic acids are used in the manufacture of polyesters, polyamides, resins, and coatings. The art teaches that cyclohexanedicarboxylic acids can be prepared by the direct hydrogenation of phthalic acids in aqueous solution over a supported rhodium catalyst.

According to Freifelder, et al., (*J. Org. Chem.* 31, 3438 (1966) phthalic acids can be hydrogenated in high yield in the presence of 5 wt. % rhodium on carbon catalyst.

U.S. Pat. No. 4,754,064 describes the use of 5 wt. % rhodium on carbon catalyst at a temperature range of 90° C. to 140° C. with the improvement of recycle of 5 to 25 wt. % of the product solution. The high cost of rhodium is a disadvantage of this method. The limited solubility of isophthalic and terephthalic acids at the low reaction temperatures is also a disadvantage in a commercial process.

U.S. Pat. No. 2,828,335 describes the hydrogenation of phthalic acid salts in high yield with good selectivity in the presence of a supported ruthenium catalyst. This patent also discloses the hydrogenation of phthalic acids using a variety of transition metal catalysts leading to extensive decarboxylation to give cyclohexanecarboxylic acid.

U.S. Pat. No. 5,118,841 and U.S. Pat. No. 5,202,475 also teach the hydrogenation of phthalic acid salts in the presence of supported ruthenium catalysts. A disadvantage to the hydrogenation of phthalic acid salts is that they must be treated with a mineral acid in order to recover the cydohexanedicarboxylic acid. The acidification procedure inherently generates a salt, which must be disposed of.

U.S. Pat. No. 3,444,237 shows the loss of selectivity and the formation of several byproducts when trimellitic acid is hydrogenated instead of the alkali salt.

The need exists for a process for the production of cyclohexanedicarboxylic acids, which is economically feasible and overcomes the deficiencies of the prior art.

SUMMARY OF THE INVENTION

The present invention relates to an improved process for the hydrogenation of phthalic acids over a supported palladium catalyst. Phthalic acids are hydrogenated with improved selectivity in aqueous solution over a supported palladium catalyst to give cyclohexanedicarboxylic acids (CHDA).

DETAILED DESCRIPTION OF THE INVENTION

It has been discovered that phthalic acids may be hydrogenated to yield cyclohexanedicarboxylic acids (CHDA) in the presence of a supported palladium catalyst. The catalyst of the present invention provides improved selectivity at optimum temperature ranges of from about 195° C. to about 230° C.; and at optimum catalyst concentration of from about 1 to about 5 wt. %. Hydrogen pressures for the practice of the invention may typically be in the range of about 600 to 700 psi, although higher pressures may be used.

Useful phthalic acids for the process of the present invention include isophthalic acid, phthalic acid, terephthalic acid, purified isophthalic acid and purified terephthalic acid. Aqueous solutions of the acids are normally used as the reactants; however, non-aqueous phthalic acids may also be used.

In a typical reaction, the desired phthalic acid is dissolved in water at the reaction temperature and contacted with a catalyst, in the presence of hydrogen. The catalyst of the present invention is a supported palladium catalyst. Useful supports include carbon, titanium dioxide and zirconium dioxide, with carbon being a more preferable support. The concentration of palladium on the support is typically in the range of from about 0.1 to about 10 weight percent. Preferably the concentration of palladium on the support is from about 0.1 to about 5; and more preferably from about 0.1 to about 1.

The process of the present invention may be carried out in a fixed bed pressurized reactor. The contact time of the solution with the catalyst depends upon the amount of catalyst employed, as is know in the art, and may range from about 0.5 hours to about 3 hours. The ratio of catalyst to substrate typically ranges from about 1:14 to 1:58 and the temperature typically ranges from about 195° C. to 260° C. The concentration of the substrate (phthalic acids) may range up to about 20 weight %. A preferred substrate concentration is 1% to 5% and a preferred temperature is 230° C. A preferred embodiment of the present invention uses a 0.5% palladium on carbon catalyst, which is inexpensive and commercially available.

Optimum rate and selectivity are achieved at about 200° C. to about 230° C. The lower temperature limit of the hydrogenation is somewhat limited by the solubility of the phthalic acids. For example, both isophthalic acid and terephthalic acid are soluble at less than 1 part per 100 parts water at 100° C. In order to efficiently operate a continuous, commercial scale reactor, the process must be operated at a temperature at which the substrate is soluble in order to avoid plugging problems and loss of catalyst through abrasion.

The yield of CHDA increases with temperature up to about 230° C.-, and shows a decrease at about 260° C., with additional by-products being formed at the higher temperatures. The selectivity to CHDA decreases as the temperature of the reaction is increased; while the selectivity to cyclohexanecarboxylic acid (CHCA) and benzoic and toluic acids increases. The selectivity to CHDA also decreases with increasing concentration of phthalic acid in the feed.

This invention can be further illustrated by the following examples of preferred embodiments thereof, although it will be understood that these examples are included merely for purposes of illustration and are not intended to limit the scope of the invention unless otherwise specifically indicated.

EXAMPLES 1–9

A one gallon titanium autoclave equipped with a drop-in catalyst basket was charged with isophthalic acid (IPA) in concentrations of from 5 wt. % to 20 wt. %; and water in such amounts that the total combined weight for IPA and water in each run was 1750 g. The catalyst basket was charged with 6.5 g of 0.5% palladium on granular carbon. The mixture was pressurized with 650 psig of hydrogen and heated to the reaction temperature. The reaction temperature was varied from 200° C. to 260° C. The mixture was stirred at temperature for 45 minutes, and the catalyst basket was dropped into the mixture. The mixture was stirred for 3 hours, cooled, and vented. The product mixture was analyzed for CHDA, IPA, CHCA, benzoic acid, and toluic acid. The results of these examples are shown in Table 1. The selectivity to a product was calculated as the moles of the product divided by the total moles of all products.

EXAMPLES 1–9

TABLE 1

Hydrogenation of IPA to 1,3-CHDA

| Ex. | Temp. | [IPA] wt % | IPA Conv. (%) | CHDA(%) | CHCA(%) | Benzoic & Toluic(%) |
|---|---|---|---|---|---|---|
| 1 | 200 | 5 | 45.0 | 98.2 | 0.6 | 1.2 |
| 2 | 230 | 5 | 54.0 | 95.7 | 2.5 | 1.9 |
| 3 | 260 | 5 | 33.7 | 91.6 | 5.0 | 3.4 |
| 4 | 200 | 10 | 27.5 | 97.5 | 0.9 | 1.6 |
| 5 | 230 | 10 | 34.9 | 93.4 | 4.1 | 2.5 |
| 6 | 260 | 10 | 34.3 | 88.8 | 7.1 | 4.0 |
| 7 | 200 | 20 | 17.0 | 97.3 | 0.9 | 1.8 |
| 8 | 230 | 20 | 28.1 | 92.6 | 4.5 | 2.9 |
| 9 | 260 | 20 | 18.3 | 91.4 | 5.4 | 3.2 |

H2 pressure - 650 psig
time - 3 hours
1750 g of reaction mixture and 6.5 g of 0.5% Pd on carbon catalyst

EXAMPLES 10–12

A one gallon titanium autoclave equipped with a drop-in catalyst basket was charged with 88 g of terephthalic acid (TPA) and 1,662 g of water. The mixture was pressurized with 650 psig of hydrogen and heated to the reaction temperature. The mixture was stirred at temperature for 45 minutes, and the catalyst basket was dropped into the mixture. The mixture was stirred for 3 hours, cooled, and vented. The product mixture was analyzed as before. The results are summarized in Table 2.

TABLE 2

Hydrogenation of TPA to 1,4-CHDA

| Ex. | Temp. | [TPA] wt % | TPA Conv. (%) | CHDA(%) | CHCA(%) | Benzoic and Toluic(%) |
|---|---|---|---|---|---|---|
| 10 | 200 | 5 | 66.5 | 98.4 | 0.1 | 1.5 |
| 11 | 230 | 5 | 61.5 | 95.3 | 0.9 | 3.8 |
| 12 | 260 | 5 | 25.3 | 85.5 | 2.3 | 12.3 |

H2 pressure - 650 psig
time - 3 hours
1750 g of reaction mixture and 6.5 g of 0.5% Pd on carbon catalyst The invention has been described in detail with particular reference to preferred embodiments thereof, but it will be understood that variations and modifications can be effected within the spirit and scope of the invention.

What is claimed is:

1. A process for the formation of cyclohexanedicarboxylic acids comprising hydrogenation of phthalic acids over a supported palladium catalyst, under hydrogenation conditions comprising temperature in the range of 195 degrees C to 260 degrees C; and hydrogen pressures in the range of 600 to 700 psi.

2. The process of claim 1 wherein the phthalic acids are selected from the group consisting of isophthalic acid, phthalic acid, terephthalic acid, purified isophthalic acid and purified terephthalic acid.

3. The process of claim 1 wherein the concentration of phthalic acids is from about 1 percent to 20 weight percent.

4. The process of claim 1 wherein the concentration of phthalic acids is from about 1 percent to about 10 weight percent.

5. The process of claim 1 wherein the concentration of phthalic acids is from about 1 percent to about 5 weight percent.

6. The process of claim 1 wherein said phthalic acids are present as aqueous solutions of phthalic acids.

* * * * *